United States Patent
Benoni

(10) Patent No.: US 10,699,804 B2
(45) Date of Patent: Jun. 30, 2020

(54) SYSTEM AND METHOD FOR THE MANAGEMENT OF PERSONAL DATA RELATIVE TO A USER BY MAINTAINING PERSONAL PRIVACY

(71) Applicant: INTERACTIVE NET BUSINESS S.R.L., Verona (IT)

(72) Inventor: Andrea Benoni, Cavaion Veonese (IT)

(73) Assignee: KATALYXER SRL, Cavaion Veronese (IT)

(*) Notice: Subject to any disclaimer, the term of this patent is extended or adjusted under 35 U.S.C. 154(b) by 232 days.

(21) Appl. No.: 15/653,706

(22) Filed: Jul. 19, 2017

(65) Prior Publication Data

US 2019/0026435 A1    Jan. 24, 2019

(51) Int. Cl.
*G16H 10/60*     (2018.01)
*H04L 29/06*     (2006.01)
(Continued)

(52) U.S. Cl.
CPC ........... *G16H 10/60* (2018.01); *G06F 19/328* (2013.01); *G06F 21/6254* (2013.01); *G06F 21/64* (2013.01); *G06Q 50/22* (2013.01); *G06Q 50/24* (2013.01); *G16H 80/00* (2018.01); *H04L 63/0421* (2013.01); *H04L 63/0435* (2013.01); *H04W 12/02* (2013.01); *H04L 63/0407* (2013.01); *H04L 67/12* (2013.01)

(58) Field of Classification Search
CPC ........ G16H 10/00; G16H 10/40; G16H 10/60; G16H 10/65; G16H 80/00; G06F 19/30; G06F 19/32; G06F 19/328; G06F 19/34; G06F 21/6245; G06F 21/6254; G06F 21/6263; G06F 21/64; H04L 63/0407; H04L 63/0421; H04L 63/0435; H04L 63/0442; H04W 12/02
See application file for complete search history.

(56) References Cited

U.S. PATENT DOCUMENTS 7,181,017 B1 * 2/2007 Nagel .................. H04L 9/0825
                                                                    380/282
2007/0245144 A1 * 10/2007 Wilson ................ G06F 21/6254
                                                                    713/170
(Continued)

FOREIGN PATENT DOCUMENTS

IT           0001327390           5/2005

*Primary Examiner* — Jung W Kim
*Assistant Examiner* — Adrian Stoica
(74) *Attorney, Agent, or Firm* — Pearne & Gordon LLP

(57) ABSTRACT

A system (1) for the management of personal data (3) relative to a user by maintaining personal privacy, comprising a Discontinuity Engine Interface (4) configured for receiving identification data (2) of the user and receiving encrypted personal data (3) of the user. The system uses separation of information domains to achieve the maximum privacy, different system components have only parts of the information as they manage information or encrypted, obfuscated or anonymous data also in combination. This separation between services and the way information are accessed permit to guarantee the maximum privacy against direct and indirect identification of the client. This level of security is permitted by pervasive cryptography starting from encapsulating data from the originator: client or analysis laboratory.

8 Claims, 3 Drawing Sheets

(51) Int. Cl.
*G06F 21/64* (2013.01)
*G16H 80/00* (2018.01)
*H04W 12/02* (2009.01)
*G06F 19/00* (2018.01)
*G06F 21/62* (2013.01)
*G06Q 50/22* (2018.01)
*G06Q 50/24* (2012.01)
*H04L 29/08* (2006.01)

(56) References Cited

U.S. PATENT DOCUMENTS

| | | |
|---|---|---|
| 2012/0029938 A1 | 2/2012 | Lauter et al. |
| 2014/0101774 A1* | 4/2014 | Armington ............. H04L 12/66 |
| | | 726/26 |
| 2014/0222684 A1* | 8/2014 | Felsher ................ G06F 19/328 |
| | | 705/50 |
| 2014/0298030 A1* | 10/2014 | Akiyama ............ H04L 63/0421 |
| | | 713/172 |
| 2016/0147945 A1* | 5/2016 | MacCarthy ......... G06F 21/6254 |
| | | 705/51 |
| 2017/0132431 A1* | 5/2017 | Gonzalez Blanco ....................... |
| | | G06F 21/6254 |
| 2017/0161439 A1* | 6/2017 | Raduchel ............ G06Q 10/063 |

* cited by examiner

SYSTEM AND METHOD FOR THE MANAGEMENT OF PERSONAL DATA RELATIVE TO A USER BY MAINTAINING PERSONAL PRIVACY

FIELD OF THE INVENTION

The present invention regards a system for the management of personal data (in particular medical data) relative to a user by maintaining personal privacy. In particular, the present invention is used when a user has to its medical information to a doctor and/or to an analysis service and/or to an insurance.

BACKGROUND

Personal privacy is a significant concern in many field and in particular in the medical field. As medical records are converted to electronic form, the risk of compromising patients' privacy increases significantly.

At the same time, electronic data are accessible to many parties, for example: analysis laboratory, doctors, insurers, hospitals, . . . .

In this context, there is a high variety of solution trying to address the problem of privacy, what usually limits the effectiveness is they miss an organic approach to anonymous and protection of information.

There are a lot of known systems having a repository on-line which combines different services creating dangerous single point of failure as a result of hacking on lacking of security policies or transparence on use of data.

Other known systems having a local archive, protect the danger of on-line system but do not face the local security problem and create limits on the capability to share data and analyze them.

An example of a known system is disclosed in document US20120029938 which describes an anonymized token given to the patient by the insures in order to ensure the coverage of the medical service for the healthcare provider and, at the same time, in order to maintain secrecy about patient identification data.

However, the system described in such a document has the drawback that it does not ensure the protection of the data in both directions of the chain (from user and from healthcare provider) especially in case of a hacking action on a part of the chain.

Scope of the invention is to overcome the above mentioned drawbacks by using a safer system and in order to guarantee both the privacy of the identification data and of the healthcare data.

SUMMARY OF THE INVENTION

The system uses separation of information domains to achieve the maximum privacy, different system components have only parts of the information as they manage information or encrypted, obfuscated or anonymous data also in combination.

The service interacting with the client (Discontinuity Engine Interface) cannot see the information as data is encrypted, who store the data (Store Services) cannot access the same as it is encrypted, who elaborate the data (Analysis Services) have no information on the owner as it is anonymized and cannot freely access the same but only the ones decided by management unit that doesn't have access to client or data.

This separation between services and the way information are accessed permit to guarantee the maximum privacy against direct and indirect identification of the client. This level of security is permitted by pervasive cryptography starting from encapsulating data from the originator: client or analysis laboratory.

Summarizing, pervasive cryptography permits to hide information except to the service that need to access them.

The connection hub is the service called Discontinuity Engine Interface (DEI), it anonymizes the user creating one or more non identifying profile (certificate) to be used to encrypt data. These profiles in conjunction with the services certificates for the various uses and/or by the services to identify request to elaborate information.

Communications are tunneled encrypted through DEI avoiding capability to identify the user from the connection, only DEI know the client and in case the identity, but cannot access the data. In this mode any attack need to break multiple services security to obtain access to information.

Discontinuity and separations of domain avoid to have any opportunity to join Identity and data or to do any deductive approach. Separation of service avoid opportunity to permit tracing of the user.

The system permits to split data in components to avoid any deductive approach to identify the user. This is the case of splitting DNA on components permitting targeted analysis based on subdomain and scope. Information non mandatory can be obfuscated to avoid any opportunity of further identification.

Temporary non identify profiles are generated to avoid capability to collect data to build client profiles by analysis services summing various information.

Actions (request of elaborate data by client) are contract based meaning that is user to decide when, what and for how long his data is manipulated. Nothing is moved without the permission of the user that channel the request through DEI that guarantee the session (workflow, quantity of data, time), not the nature of data that is defined by Management unit. Primarily DEI and Management unit guarantee the respect of the task contract, secondarily all other services check the respect of the requests according to the Client Task Contract (CTC) details.

BRIEF DESCRIPTION OF THE DRAWINGS

The present invention is illustrated by way of example and not limited in the accompanying figures in which like reference number are indicated.

DETAILED DESCRIPTION

Figure 1:
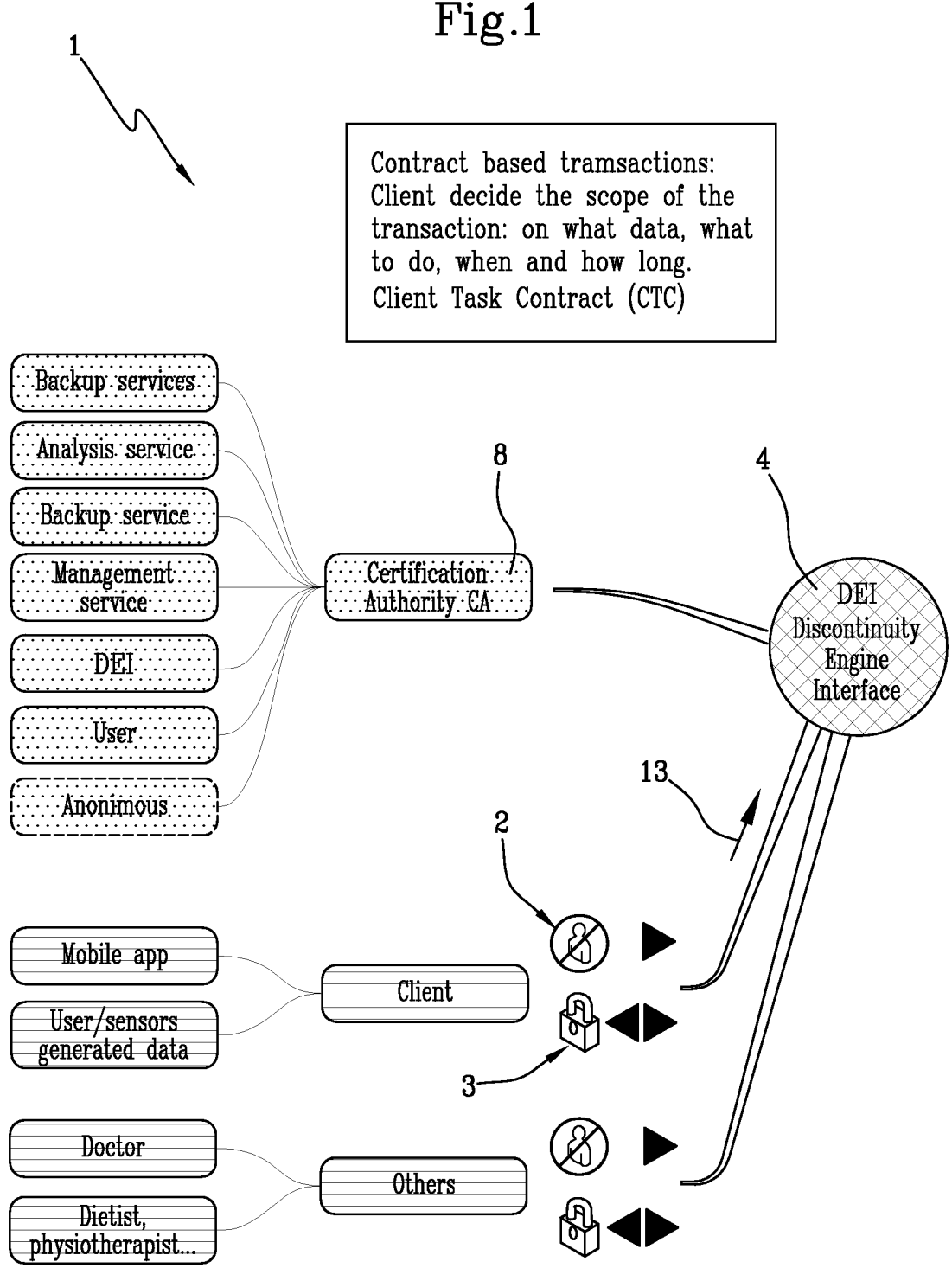
FIG. 1 is a first part of the block diagram showing the system of the present invention on the side of the user.
Figure 2:
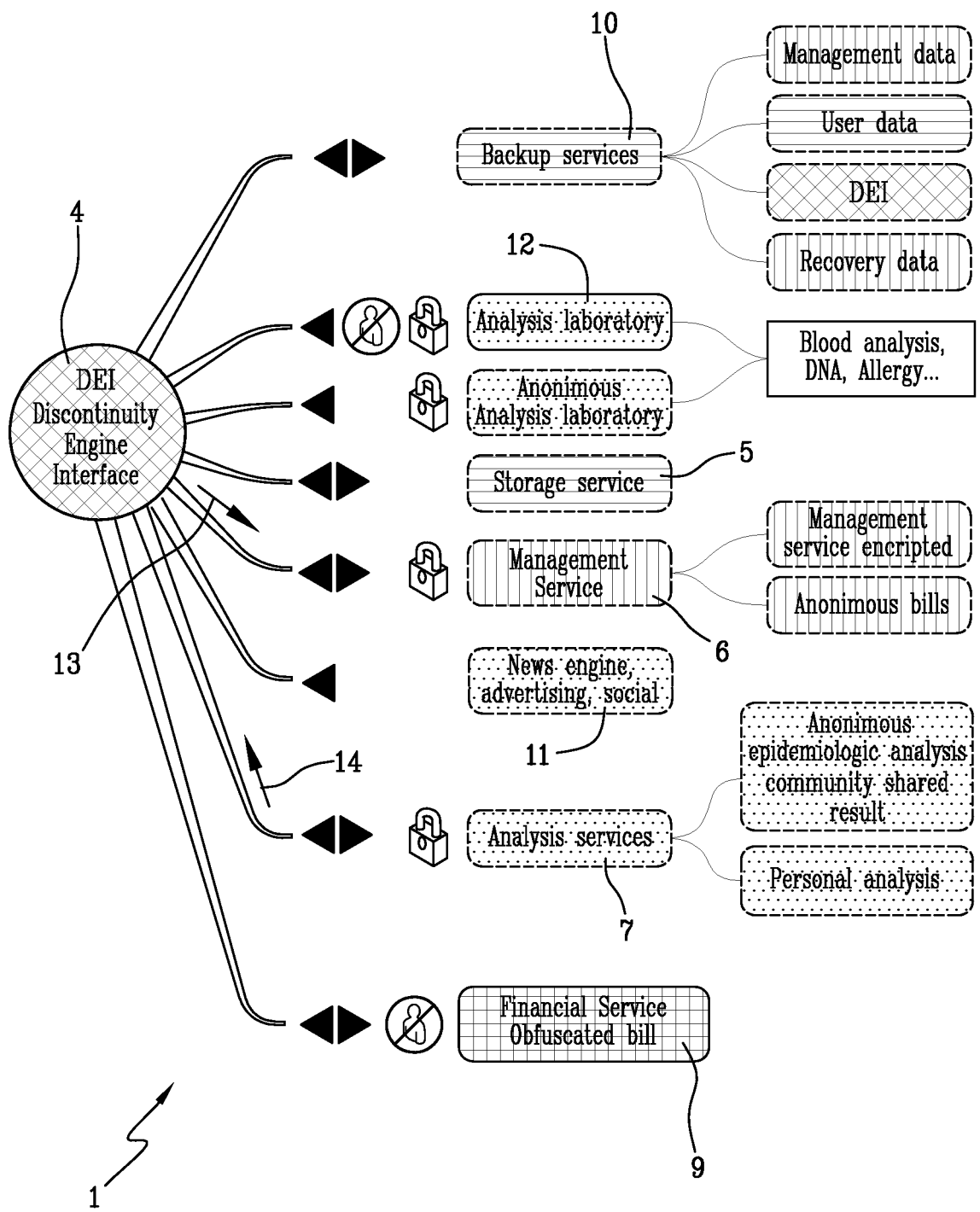
FIG. 2 is a second and continued part of the block diagram of FIG. 1 showing the system of the present invention on the side of the services.
Figure 3:
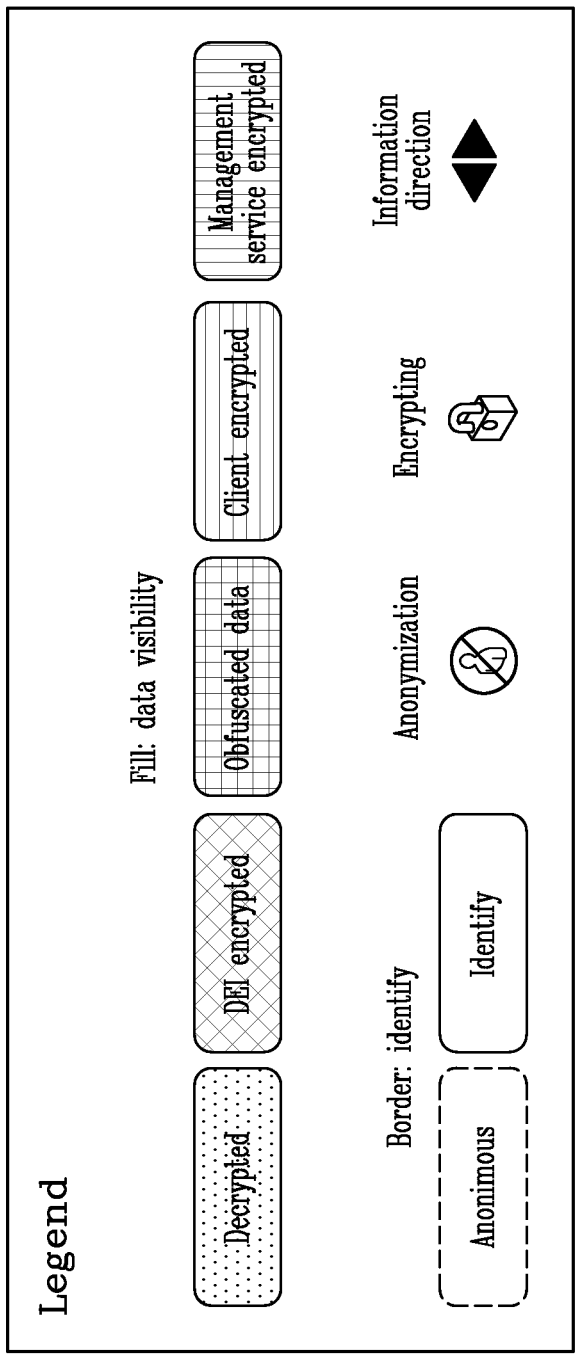
FIG. 3 shows a legend referred to FIGS. 1 and 2.

The system 1 object of the present invention is configured to treats two kinds of data: identification data 2 of the user (for example name, surname, address, . . . ) and personal data 3 of the user (for example healthcare data, . . . ).

The system 1 comprises the following units:

a Discontinuity Engine Interface 4 (DEI) configured for connecting users to the management unit and/or services units, anonymizing connections and tunneling data. DEI manages all communications between services without accessing data encrypted (only tunneling)

based on client task contract. In other words, DEI is configured for anonymizing all action of the user on the system 1;

Storage Service 5 (SS) configured for archiving data, anonymizing data encrypted, subdividing data. Note that SS is separated from Analysis Service and both are separated from Management Unit. In the Storage Service 5 data is divided in chuck and there is no way to know who belongs, only Management unit is configured to maintains the link between the personal data 3 and the anonymous identity profile. Storage Service 5s gives data only to DEI which manages data for sending it to Analysis Services (in this mode an analyzer see only temporary the data for the scope required);

Management Unit 6 (MU) configured for managing lists of data and elaboration requests. It is not configured for archiving data, but it sends requests through DEI to move data to the requested service unit by client task contract. In practical, MU maintains the list of available data for each user identity profile, it can work with anonymous or real identity profile of the user according to the level of privacy the client wants to achieve. In all cases MU has not access to the personal data 3 itself;

Analysis Service 7 (AS) configured for elaborating anonymized data received by Storage Service 5s through DEI. In other words, Analysis Service 7 cannot read directly the personal data 3, but it receives personal data 3 from DEI based on the request of the user to the Management Unit 6. Results of the Analysis Service 7 is sent to the client in a return signal trough DEI and it can be read only by user and stored encrypted on Storage Service 5;

Certification Authority 8 (CA) configured for maintaining identification information of the user and for generating anonymous certificates. In other words, CA conserves multiple certificates: services certificates, personal certificates identifying and anonymous. Personal identify and anonymous certificates apply to user and doctors avoiding any opportunity to trace information flow. Service certificates guarantee that only the defined service can access the encrypted information;

Financial Service 9 (FS) configured for generating a bill (FS can be part of the DEI or it can be separated from DEI). In other words, FS knows the identity of the user which pays the bill, but the cost items of the bill are obfuscated to avoid privacy problems.

Further, below will be cited other services (optional services) which are:

Backup Service 10 (BS) configured for performing a backup of the management data, user data, DEI actions in order to recover data;

Information Service 11 (IS) configured for providing additional information from external sources;

Analysis Laboratory 12 (AL) configured for working on anonymous profiles (AAL) and for inserting data directly in the system 1 through DEI.

Please note that all units/services can be single or multiple. Advantageously, this will allow to offer different options on Analysis Service 7s in competition for quality, features or cost. The model remains the same, DEI and Management Unit 6 will put in communication and control available services.

According to the present invention, the DEI is configured for receiving identification data 2 of the user and receiving encrypted personal data 3 of the user.

Then, DEI generates an anonymous virtual certificate associated to the identification data 2 of the user and associates encrypted user personal data 3 to the anonymous certificate.

DEI generates an information signal containing encrypted user personal data 3 and the anonymous certificate.

The MU receives the information signal from the Discontinuity Engine Interface 4 and receives a management request signal 13 from the user through Discontinuity Engine Interface 4. In functions of these requests, MU manages the encrypted user personal data 3 in function of the content of said management signal.

The service unit (which could be the Analysis Service 7, Financial Service 9, Storage Service 5, ... ) is configured for receiving a signal containing the encrypted user personal data 3 from the Management Unit 6 under a request contained in the management signal, and for carrying out one or more operations on the encrypted user personal data 3 (for example analysis, ... ).

Then, Service Unit generates a return signal as a result of the operations carried out and sends it to the Management Unit 6. DEI is configured for requesting to the Management Unit 6 the data contained in the return signal and to send them to the user to which correspond the anonymous certificate.

Here below are reported some examples of use of the system 1 object of the present invention.

Online Analysis

A user registers himself on DEI obtaining two certificates, the one Public and the one anonymized.

User collects personal data 3 (healthcare data) from various source, encrypts it and send it through DEI to the Storage Service 5. Neither DEI or Storage Service 5 can access the personal data 3. Information about data nature is encrypted and the personal data 3 are sent to Management Unit 6. Only this unit can decrypt and manage the data.

When the user asks any kind of elaboration, an encrypted request is forwarded by DEI to the Management Unit 6 which generates one or more requests of data channeled through DEI to the Storage Service 5 (for getting the stored personal data 3) and then to the Analysis Service 7. Neither DEI and the Storage Service 5 can decrypt the personal data 3, just the Analysis Service 7. The results are encrypted, if defined by the request of the user (CTC), and the results return to the client through DEI or are stored in the Storage Service 5.

Only User can read the results, if defined by a Request Actions Contract the results can be stored and this case will remain encrypted until the next use by an Analysis Service 7 or qualified third party (Doctors ... ) in all cases after request by the user to Management Unit 6.

Online analysis could be detailed in four workflows here below reported.

Flow 1: User archiving on-line health-related data (legend for some terms is below reported after flows).

1. User collects data using an electronic device, inserting or digitalizing information or directly from sensors, attended or unattended (manual or automatic collection of data and upload).

2. An user application removes identifying information, subdivide data into single pieces of information.

Every Data element (piece of information) is a User Data Envelope composed by data, Metadata description and a Signed checksum (CRC) to guarantee data integrity. Signed checksum is made using anonymous user profile to protect privacy pervasively in all uses. App then encrypts the envelope using Differentiate Encrypting key.

Granularity is optimized to guarantee segregated data access and security, and an example could be information about DNA that are subdivided in single Elements to be accessed individually or in subset. The app subdivides information permitting strictly to use the needed subset on the following elaboration. The Differentiate key is the combination of Unique Information Id assigned to the data and a User secret key. The algorithm does not permit to recreate the specific Differentiate Encrypting Key (DEK) without knowing the User DEK generation key. In this mode, User can in future recreate the access key when needed and the same time the secret key cannot be deducted. The algorithm generates the Unique Information Id from a random sequence guarantees the uniqueness across all users as well the anonymity of the Id to avoid the capability to connect single pieces of information to the anonymous profile.

3. The user connects to DEI using an identifying certificate or an anonymous certificate. DEI can also just interact with the user anonymous certificate. The only exception is the procedure for recovering the cryptographic keys that is managed differently.
4. DEI generate a session ID used in all following communications performed in the same session.
5. The user generates a request Archive meta-data structure including type, nature, and quantity of data, and all signed checksum of the encrypted information to archive with the Unique Information Id (UIID) for each piece of information. All future reference of data will be related to UIID. User encrypts the request using the Management Unit 6 certificate, only MS can access to the metadata information collection.

User sends the request to Management Unit 6 using DEI.
6. DEI forward the request to Management Unit 6.
7. Management Unit 6 stores Archive meta-data: UUId, data type, and nature, signed checksum of the encrypted Envelops.
8. Management Unit 6 generates Atomic requests including UUId and checksums signed with MS certificate for each Envelope to avoid any link to Anonymous User Id.

Management Unit 6 generates instructions for DEI with the list of Atomic requests and Archiving session, signs the request and send it.

The same signed list of pairs of UIID and signed checksum are sent to User App to provide during archiving through DEI.
9. User App re-encrypt Envelop using Archive Service certificate sending together with Atomic request information through DEI to Archive Service. The scope of re-encryption is securely protecting Envelops giving access only to Archive Service.
10. DEI forwards the information to Archive Service DEI control just there is a certified request from User and do just a quantity and timeout control over the session based on User/Management Unit 6 specifications
11. Archive Service check correspondence of data with signed checksum received from Management Unit 6, archive data using the UIID and send acknowledge to DEI and through DEI to, Management Unit 6, and User. The acknowledge close the cycle for each information (Atomic request)

Flow 2: Reporting and analysis
1. User contacts Management Unit 6 through DEI. All requests are encrypted using the Management Unit 6 Cryptographic certificate. The first action is a request for a Session Id and the List of Unique Information Ids to Management Unit 6 for analysis on the data or a subset.
2. Management Unit 6, using destination certificate, generates:
   a. An encrypted request with the Session-Id and Unique Information Id list for the Storage Service 5;
   b. An encrypted request with Session-Id and Quantity and Timeout for DEI,
   c. An encrypted request with characteristics of data, type of request for Analysis Service 7.
3. DEI establishes a Session framework based on the time and quantity limits requested by Management Unit 6.
4. User encrypts the list of Differentiate encrypting keys to access the pieces of data involved in the Analysis with the Certificate of Analysis Service 7 and information about the Session Id.
5. User sends the encrypted envelope through DEI to Analysis Service 7.
6. DEI forwards all requests to the Management Unit 6 or Services controlling the respect of Session framework policies. DEI cannot access the passwords to access data and neither data itself.
7. Storage Service 5 forwards through DEI the User Data Envelops identified by List of Unique Information Ids to Analysis Service 7. Re-encrypt data using Analysis Service 7 certificate.
8. DEI controls the quantity and the request time is correct with respect to a Session Id, forward data to Analysis Service 7.
9. Analysis Service 7 receives data, decrypt it the first time using his certificate and decrypt internal data with the Differentiate Encrypting key list received encrypted from user.
10. Analysis Service 7:
    a. Execute requested analysis in a secure environment that guarantee complete isolation. No key and decrypted data are permanently archived or communicated externally;
    b. If results are requested to Storage Service 5, Storage Service 5 re-encrypt using Storage Service 5 certificate and submit through DEI to it
    c. Encrypt results using user certificate and return to the user by using DEI.
11. User receives Analysis Service 7 results encrypted trough DEI. The User application can decrypt, read and store the encrypted results.

Flow 3: Laboratory blood analysis with anonym profile
1. Laboratory just knows the anonymous profile of the user.
2. Laboratory sends anonymous results of analysis encrypted using the anonymous user certificate to user through DEI.
3. The User asks through DEI to Management Unit 6 to create a session for archiving data. Only Management Unit 6 knows the nature of the data and their Id, but not the identity of the user. DEI just controls that there is a certified request from the User and just control a quantity and timeout control over the session.
4. The User using Session Id archives data through DEI in the Storage Service 5.

User uses Asymmetrical certificate to re-encrypt data for Storage Service 5 and link to Session Id. User fragments Data without reference to Anonymous or Identity Id, only to Session Id and Segment data Id.

Flow 4: Laboratory blood analysis with identity
1. Laboratory knows the profile of the user.
2. Laboratory anonymizes the results of analysis.
3. Laboratory sends anonymous result of analysis encrypted using the anonymous user certificate to user through DEI.
4. User asks through DEI to Management Unit 6 to create a session for archiving data. Only Management Unit 6 knows the nature of the data and their Id, not the identity of the user. DEI controls just that there is a certified request from User and perform a quantity and timeout control over the session.

Another example of use of the system 1 object of the present invention is represented by the doctor interactions.

Doctor Interactions

Guest accesses the Encrypted list of available information through DEI to Management Unit 6, DEI have no access to data. The guest defines the contract containing the material he wants to share with the doctor, send Encrypted request to the Management Unit 6 and asks DEI to establish a contract session where is defined Source (Storage), List (Management Unit 6), Destination (Doctor), Quantity times and expiry.

DEI channels the encrypted request to Storage and result to Doctor. Doctor receives data using his anonymized profile.

Doctor interactions could be detailed in workflow here below reported

Flow 5: Doctor interaction
1. User through the Management Unit 6 Cryptographic certificate asks a Session Id and Segment Ids to the Management Unit 6 for review on the data. User encrypts cryptography key using Doctor Certificate to permit only to him the access.
2. Management Unit 6 generate:
   a. An encrypted request with the Session Id and Data Segment Id for the Storage Service 5.
   b. An encrypted request with Session Id and Quantity and Timeout for DEI.
   c. An encrypted request with characteristics of data, type of request for Doctor
3. User encrypts the password/s to access the pieces of data involved in the Analysis with the certificate of Doctor and information about the Session Id
4. DEI forwards all request accessing only the one addressed to the same service. DEI cannot access the password to access data and neither data itself.
5. Storage Service 5 forwards through DEI the data to Doctor. Storage Service 5 re-encrypts data using Doctor anonymous certificate.
6. DEI controls the quantity and the request time in respect of a predefined to Session Id. DEI forwards data to Doctor.
7. Doctor receives data, decrypts it using his certificate, decrypt internal data with the password received encrypted from user.

A third example of use of the system 1 object of the present invention is represented by the Anonymous epidemiologic analysis.

Anonymous Epidemiologic Analysis, Community Shared Result

Client can decide to participate to epidemiologic analysis in part of its data, the only information needed. Example genre, age, habitudes, values and analysis.

Client decides times and modes of the participation and can take advantages of the result.

It has to be noted that in the workflows above mentioned
- all subjects have asymmetrical cryptographic certificate permitting to receive dedicated secure communications or certify submittals;
- only DEI is in contact with user using an identify profile or anonymous (identify profile is not mandatory);
- all other services use user anonymous profile except Financial Service 9s, in this case user use Identity profile but the information is shared and information about the nature of services obfuscated;
- in neither case if one single system 1 is hacked there is capability to access data and identity at the same time. Also accessibility to data is fragmented and difficult to connect to profile also anonymous;
- in the registration of the user, use of identifying identity is not mandatory, it can be used an anonymous profile;
- request to Certification Authority 8 of one or multiple anonymous certificates, request and delivery are secured to avoid any identity steal or recognition.

Here below is reported a "legend" with reference to the terms above mentioned in the workflow examples.

User application: application available for mobile devices, computer, kiosk, sensors or other devices permitting to load monitored, with user interaction or in automatic the data. In particular, the automatic devices use the same rules with an initial setup that protect user secret key with the support of the state of art encryption hardware support. A lightweight version of the app will be available also for web browser and other interfaces with a specific process to guarantee security.

Data element: a single piece of information that can be used alone or in join with others. Data is subdivided into single elements to avoid misuse of information or reverse search. One example is DNA information where single elements can be combined to reach complete identifying profiles, splitting information permit to get the target without undesirable and unneeded exchange of information.

Metadata descriptor: contains information about the data permitting to elaborate when requested. Descriptions are tuned to focus on just the target and avoid to permit to deduct any identify data, for this reason, the descriptors just focus on the future elaboration of the same and not the archiving that is a separate set of meta-data managed only by Management Unit 6.

Data-element: any information (digitalized data, notes, sensor data, photo, audio . . . ).

User-Data-Envelope: is the encrypted structure of data containing Data-element and Meta-data descriptor and a signed checksum (CRC) to guarantee data integrity, signed using anonymous user profile to protect privacy pervasively in all uses. The envelope is identified only by the Unique Information Id.

Unique Information Id (UUId): is the code that identifies uniquely respect all the data in the system 1 the single User Data Envelope. A specific algorithm guarantees the uniqueness and the anonymous.

User DEK generation key: the encrypting key the user uses to generate the encryption key specific for each data element. Only the user knows the key; the same can be securely archive in the local repository of the user mobile app. The system 1 has provision to recover the key with user interaction securely.

Differentiate encrypting key (DEK): encrypting key calculated from generation user key and data element Unique Identifier. The key can be generated only from the user that is the only one that knows the generation key.

Archive meta-data: a subset of the information permitting to process securely envelope requests based on user interaction indirectly. Information is limited to the minimum to permit management including type Archiving session: an archive session identifier shared between the user, DEI and Management Unit 6 to manage in security the storage controlling all steps between the subjects.

Atom requests: include UUId and checksums signed with MS certificate for each User Data Envelope Session Id: Unique identifier of a session assigned by a service based on a request.

List of Unique Information Ids: List of UIID specifying the data needed for the requested analysis or elaboration.

Session framework: permit a DEI to limit traffic between services inside specific session policies like: time, quantity, subjects in communication.

It has to be noted that the cryptograph actions above mentioned are preferably performed by using the techniques contained in the Italian patent 0001327390 (Appl. Number. VR2001A000013) filed in the name of the same Applicant. In particular the content of the patent above cited is here recalled back for the encrypting/decrypting actions.

It is also object of the present invention a method for managing personal data 3 relative to a user by maintaining personal privacy. In particular, the method is performed by actuating the phases above described in relation to the system 1 and here recalled.

In particular the method is performed by at least one electronic processor in a computing environment comprising the web (internet), servers connected to the web and electronic devices.

The present invention reaches the scope initially placed.

In particular, the system 1 defines a data exchange structure in which who know the user identity cannot access the data, and doesn't know data nature.

The system 1 can work also with just anonymous profiles

Who elaborate the data receive anonymous pieces of information just when required and not store permanently the same.

Who store the data doesn't know the user (owner) and cannot access the data and doesn't know data nature.

Who delivers data cannot access the same or generate the command to retrieve it.

Who manage the requests cannot access data or delivery data.

Who manage the requests know only the anonymous profile

The user has complete continue control over the data through encryption and managing requests to DEI and Managing Service.

The invention claimed is:

1. System (1) for the management of personal data (3) relative to a user by maintaining personal privacy, comprising:
   a Discontinuity Engine Interface (4) configured for:
   receiving identification data (2) of the user;
   receiving encrypted personal data (3) of the user;
   generating a unique anonymous virtual certificate associated to the identification data (2) of the user;
   associating encrypted user personal data (3) to the unique anonymous certificate;
   generating an information signal containing encrypted user personal data (3) and the unique anonymous certificate;
   a Management Unit (6) configured for:
   receiving the information signal from the Discontinuity Engine Interface (4);
   receiving a management request signal (13) from the user through Discontinuity Engine Interface (4);
   managing the encrypted user personal data (3) in function of the content of said management signal;
   maintaining a link between the personal data (3) and the unique anonymous virtual certificate without having access to the personal data (3) itself;
   a service unit configured for:
   receiving a signal containing the encrypted user personal data (3) from the Management Unit (6) under a request contained in the management signal;
   carrying out one or more operations on the encrypted user personal data (3);
   generating a return signal (14) as a result of the operations carried out and sending it to the Management Unit (6);
   said Discontinuity Engine Interface (4) being configured for requesting to the Management Unit (6) the data contained in the return signal (14) and to send them to the user to which correspond the unique anonymous certificate;
   wherein the service unit comprises a Storage Service (5) for storing the user personal data (3) received from the Management Unit (6);
   said service unit further comprises an Analysis Service (7) configured for: decrypting the user personal data (3) received from the Management Unit (6);
   receiving a decrypting/encrypting certificate from the user and to decrypt data contained in the return signal (14) using said certificate;
   analyzing the decrypted user personal data (3) received from the Management Unit (6) and adding further data to the personal data (3) resulting from an elaboration of the user personal data (3) itself performed by the analysis service;
   generating an encrypted return signal (14) as a function of the analysis performed by using said certificate;
   wherein Discontinuity Engine Interface (4) cannot access personal data (3) of the user, Storage Services (5) cannot access personal data (3) of the user, Analysis Service (7) cannot access the identification data (2) of the user as it is anonymized, and Management Unit (6) cannot access personal data (3) and the identification data (2) of the user.

2. System (1) according to claim 1, wherein the Analysis Service (7) comprises a laboratory of medical matters.

3. System (1) according to claim 1 wherein the Discontinuity Engine Interface (4) is configured to generate also an anonymous virtual certificate of the user through a certification unit connected to the Discontinuity Engine Interface (4) and configured to receive a signal containing information relative to the true identity profile of the user and to store them.

4. System (1) according to claim 1 further comprising a Financial Service (9) configured to receive the return signal (14) from the service unit and to generate a corresponding bill in function of the contents of the return signal (14).

5. Method for managing personal data (3) relative to a user by maintaining personal privacy, comprising the following phases:
   sending identification data (2) of the user from the user to a Discontinuity Engine Interface (4) for registering identification data (2) of the user;
   sending encrypted personal data (3) of the user from the user to a Discontinuity Engine Interface (4) for registering personal data (3) of the user;

generating, through the Discontinuity Engine Interface (4), a unique anonymous virtual certificate associated to the identification data (2) of the user;

associating, through the Discontinuity Engine Interface (4), user personal data (3) to the unique anonymous certificate and generating an information signal containing the user personal data (3) and the unique anonymous certificate;

managing the content of the information signal through a Management Unit (6) in function of the requests received from the user;

maintaining a link between the personal data (3) and the unique anonymous certificate through a Management Unit (6) which has no access to the personal data (3) itself;

carrying out one or more operations on the content of the information signal through a service unit in function of the requests received from the user;

generating a return signal (14) by the service unit as a result of the operations carried out and sending it to the Management Unit (6);

sending the data contained in the return signal (14) to the user to which correspond the unique anonymous certificate through the Discontinuity Engine Interface (4);

storing the user personal data (3) received from the Management Unit (6) in a Storage Service (5);

decrypting the user personal data (3) received from the Management Unit (6) through an Analysis Service (7) which is configured for performing the following steps;

analyzing the decrypted user personal data (3) received from the Management Unit (6);

generating an encrypted return signal (14) as a function of the analysis performed;

receiving a decrypting/encrypting certificate from the user and to encrypt data contained in the return signal (14) using said certificate;

analyzing the decrypted user personal data (3) received from the Management Unit (6) and adding further data to the personal data (3) resulting from an elaboration of the user personal data (3) itself performed by the Analysis Service (7);

generating an encrypted return signal (14) as a function of the analysis performed by using said certificate;

wherein Discontinuity Engine Interface (4) cannot access personal data (3) of the user, Storage Services (5) cannot access personal data (3) of the user, Analysis Service (7) cannot access the identification data (2) of the user as it is anonymized, and Management Unit (6) cannot access personal data (3) and the identification data (2) of the user.

6. Method according to claim 5 wherein the step of analyzing the user personal data (3) comprises a medical analysis in a laboratory.

7. Method according to claim 5, characterized in that the step of generating the anonymous virtual certificate of the user is performed through a certification unit connected to the Discontinuity Engine Interface (4) and configured to receive a signal containing information relative to the true identity profile of the user and to store them.

8. Method according to claim 7 further comprising a step of generating a corresponding bill in function of the contents of the return signal (14).

* * * * *